United States Patent [19]

Muhr

[11] Patent Number: 5,545,762

[45] Date of Patent: Aug. 13, 1996

[54] PROCESS FOR PREPARING 1-CYCLOPROPYLALKANE-1,3-DIONES

[75] Inventor: Jürgen Muhr, Alfter, Germany

[73] Assignee: Huels Aktiengesellschaft, Marl, Germany

[21] Appl. No.: 326,371

[22] Filed: Oct. 20, 1994

[30] Foreign Application Priority Data

Feb. 9, 1994 [DE] Germany .................. 44 04 059.8

[51] Int. Cl.⁶ ................................. C07C 45/45
[52] U.S. Cl. ................ 568/346; 568/314; 568/388
[58] Field of Search .................. 568/314, 346, 568/388

[56] References Cited

U.S. PATENT DOCUMENTS

| | | | |
|---|---|---|---|
| 3,507,958 | 4/1970 | Zimmermann | 568/346 |
| 4,256,657 | 3/1981 | Wheeler | 568/346 |
| 5,015,777 | 5/1991 | Chisolm et al. | 568/314 |
| 5,118,681 | 6/1992 | Amick et al. | 514/616 |
| 5,344,992 | 9/1994 | Drewes et al. | 568/314 |

FOREIGN PATENT DOCUMENTS

| | | |
|---|---|---|
| 0410726 | 1/1991 | European Pat. Off. . |
| 0454624 | 10/1991 | European Pat. Off. . |

OTHER PUBLICATIONS

Journal of Organic Chemistry, vol. 17, pp. 685–688, 1952, George W. Cannon, et al., "Actylation Studies. I. Methyl Cyclopropyl Ketone".

*Primary Examiner*—James H. Reamer
*Attorney, Agent, or Firm*—Oblon, Spivak, McClelland, Maier, & Neustadt, P.C.

[57] ABSTRACT

1-cyclopropylalkane-1,3-diones are prepared by reacting a cyclopropyl alkyl ketone with a carboxylic ester in the presence of an alkali metal alcoholate, at temperatures of not more than 50° C. in the presence of a solvent which is free of alcohol or contains only small quantities of alcohol.

20 Claims, No Drawings

PROCESS FOR PREPARING 1-CYCLOPROPYLALKANE-1,3-DIONES

BACKGROUND OF THE INVENTION

1. Field of the Invention

The invention relates to a process for preparing 1-cyclopropylalkane-1,3-diones from an alkali metal alcoholate, a carboxylic ester having at least one hydrogen atom on the alpha carbon of the carboxylic acid skeleton, and a cyclopropyl alkyl ketone.

2. Discussion of the Background

Cyclopropylalkane-1,3-diones are precursors of numerous pesticides. It is known in the literature to prepare cyclopropylalkane-1,3-diones from cyclopropyl alkyl ketones and carboxylic acid derivatives, with the carboxylic acid species which are most reactive, such as for example, acetic anhydride or acetyl chloride, being reacted with, for example cyclopropyl methyl ketone (CPMK), and the reaction being carried out in the presence of aggressive catalysts or auxiliary substances, e.g. $BF_3$ (U.S. Pat. No. 3,507,958).

The use of acetyl chloride or $BF_3$ in industrial processes is associated with a particularly high degree of technical complexity owing to the highly toxic and strongly corrosive properties of these hydrolysis sensitive chemicals and their decomposition products.

Carboxylic esters, such as for example ethyl acetate, represent suitable synthesis partners for the cyclopropyl alkyl ketone, for example CPMK, which can be handled more easily and the use of which is associated with a significantly lower hazard potential. However, the corresponding condensations were hitherto achieved using the strongest possible bases, such as, for example, sodium hydride (U.S. Pat. No. 3,507,958) or sodium amide (Cannon and Widden, J. Org. Chem. 17,685 (1952)), with the yields being relatively unsatisfactory, i.e. from about 40 to 75% of theory.

The use of sodium amide and sodium hydride naturally involves substantial risks, since explosive products form in the presence of moisture, air and carbon dioxide, and, therefore, necessitates extensive safety precautions.

In addition to this, the syntheses carried out using sodium hydride are typically associated with uneconomical space/time yields, with reaction times of up to 14 hours.

It appears from EP-A-0 410 726 that there is no benefit in dispensing with such strong bases and replacing them, for example, with less basic alkali metal alcoholates of lower alcohols, such as, for example, sodium methoxide or sodium ethoxide. According to this reference, reaction of CPMK and ethyl acetate together with sodium methoxide only achieves a yield of about 21% of theory and a grade of 75%, even when the condensation is carried out at high temperatures. The alcohol is continuously distilled off from the reaction mixture in order to displace the equilibrium, and in addition to this, the ethyl acetate is employed in a large excess. In order to separate off the byproducts, a filtration step is required which is elaborate for an industrial manufacturing process and in which effective precipitation is not achieved at a purity of 75%, thereby necessitating additional work-up steps before the product can be marketed. The unsatisfactory yields not only represent an economic problem, but must also be criticized from the ecological point of view since it is necessary to dispose of relatively large quantities of byproducts.

SUMMARY OF THE INVENTION

Accordingly, one object of this invention is a process which avoids the disadvantages of prior processes and supplies 1-cyclopropylalkane-1,3-diones in high yield using simple bases.

According to the invention, this object is achieved by reaction of carboxylic esters of formula I with alcoholates of formula II and cyclopropyl ketones of formula III to form the 1-cyclopropyl-alkane-1,3-diones of formula IV according to the reaction scheme

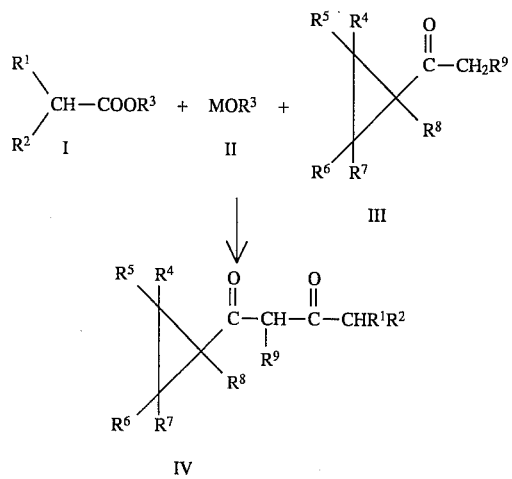

where $R^1$, $R^2$ and $R^4$ to $R^8$ are, independently, hydrogen, alkyl having from 1 to 6 carbon atoms or an optionally substituted aryl group having from 6 to 10 carbon atoms, $R^3$ is an alkyl group having from 1 to 10 carbon atoms, M is an alkali metal, and $R^9$ is hydrogen or alkyl having from 1 to 20 carbon atoms, carrying out the reaction at temperatures of less than 50° C. in a solvent which is free of alcohol or contains only up to 0.7 mol of alcohol per mol of alcoholate.

Owing to the lower reactivity of the alkali metal alcoholates as compared with alkali metal hydrides and amides, it was to be expected, as can be deduced from EP-A-0 410 726, that the desired condensation reaction would only occur at relatively high temperatures. Contrary to this expectation, synthesis using alkali metal alcoholates is successfully achieved at significantly lower temperatures, preferably in the range between −20° C. and 50° C., in high yields, without measures being taken to displace the reaction equilibrium by feeding in excess starting compounds and separating off alcohol arising during the reaction.

The substituents $R^1$, $R^2$ and $R^4$ to $R^8$ can be alkyl groups, for example methyl, ethyl, propyl, isopropyl, n-butyl, isobutyl or hexyl. The alkyl groups can be branched or straight-chain, cyclic, saturated or olefinically unsaturated. Two of the substituents in each case can also be bonded to each other to form an optionally substituted cycloalkyl group. $R^1$ and $R^2$ are preferably hydrogen.

The optional substituents on groups $R^1$–$R^2$ and $R^4$–$R^8$ may be any substituent which does not adversely affect the reaction to form the desired cyclopropylalkane-1,3-diones. Such substituents are generally inert to the reaction conditions of the condensation reaction. Suitable substituents include alkyl groups having 1–6 carbon atoms, alkoxy groups having 1–10 carbon atoms and mononuclear (preferably hydrocarbon) aryl groups having 6–10 carbon atoms.

Examples of alkyl groups for $R^3$ are methyl, ethyl, isopropyl, butyl, hexyl and octyl. $R^3$ is preferably an alkyl group having from 1 to 6 carbon atoms, in particular methyl or ethyl.

Lithium, sodium, potassium, rubidium and cesium are suitable alkali metals. In this context, sodium and potassium are preferred.

In addition to hydrogen, $R^9$ may be methyl, ethyl, butyl, t-butyl, ethylhexyl or dodecyl, for example. In general, the alkyl groups can be saturated or olefinic, branched, straight-chain or cyclic. $R^9$ can also be optionally substituted by mononuclear aryl, preferably $C_{6-10}$ aryl, or alkoxy, preferably $C_{1-10}$ alkoxy.

In a preferred embodiment of the invention, $R^4$ to $R^9$ are hydrogen, i.e. the compound of formula III is CPMK.

The acylation of the cyclopropyl ketones with the carboxylic esters is particularly preferably effected at temperatures of from 0° to 40° C.

Based on 1 mol of cyclopropyl ketone, preferably from 1 to 5 mol, and particularly preferably from 1 to 2 mol, of alkali metal alcoholate and from 1 to 9 mol, preferably from 1 to 2 mol, of carboxylic ester are introduced for the synthesis.

Preferably, the methoxide or the ethoxide of potassium or sodium are used as the alkali metal alcoholate.

According to the invention, the reaction is carried out in the presence of a solvent which either does not contain any alcohols or only contains trivial quantities of alcohols. Solvents are preferred which are relatively immiscible with water and which can be used as extracting agents during the work-up. In principle, all those solvents which are inert towards the starting compounds are suitable, such as for example, aromatic, aliphatic and/or araliphatic hydrocarbons, aromatic halohydrocarbons, ethers or polyethers, esters which are resistant to re-esterification or hydrolysis, amides and amines. It is very much preferred that ethers, particularly tert-butyl methyl ether, be employed.

In order to simplify the work-up, it is preferable to use no foreign solvents in the process of the invention. This is achieved by carrying out the reaction in excess quantities of starting compounds which act as solvent, preferably employing the ester used for the acylation.

Alcohol is not suitable for use as a reaction medium or for addition in quantities which would be introduced, for example, when using the 20 to 30 wt. % alcoholate solutions which are customarily available in the trade. In these quantities, alcohol inhibits the reaction. Small additions of up to 0.7 mol of an alcohol per mol of alkali metal alcoholate are permissible as an additive without appreciably lowering the yield.

Such additives can have a positive effect with regard to the rheological properties of the reaction mixture. Especially on an industrial scale, this can mean an increase in the space/time yield as a result of a more concentrated mode of operation and a minimized operational risk as the result of a more efficacious heat distribution. Branched and/or straight-chain aliphatic (preferably $C_{1-10}$ aliphatic) and araliphatic (preferably $C_{7-15}$ araliphatic) alcohols, such as, for example, tert-butanol and poly $C_{2-4}$ alkylene glycols, such as polyethylene glycols, and their ethers (preferably $C_{1-6}$ alkylethers), in particular diethylene glycol dimethyl ether, are suitable for use as additives.

A particularly preferred product of the invention is 1-cyclopropylbutane-1,3-dione in which $R^1$, $R^2$ and $R^4$ to $R^9$ are hydrogen. This product is obtained by acylating CPMK using an acetic ester, preferably the methyl or ethyl ester, and using a sodium or potassium alcoholate, in particular using the methoxide or ethoxide.

When the CPMK is acylated with acetic esters, the resulting alcohol need not be distilled off, since such a procedure inevitably leads to depletion of the low boiling ester component, thereby minimizing the yield. Moreover, distillation within the indicated temperature range requires a considerable increase in the amount of apparatus employed since, in the first place, this distillation would have to be carried out in vacuo with the efficiency of separation being poor. In the second place, recovery of the ester which has been inadvertently distilled off necessitates additional apparatus and expense.

The process may be carried out either continuously, for example in a continuous tubular-flow reactor, or batchwise in a discontinuous stirred-tank reactor.

In the process of the invention, the 1-cyclopropylalkane-1,3-diones occur initially as enolates and may be isolated in this form, for example by filtration or after having distilled off volatile constituents, and can be liberated therefrom by acidification in accordance with known methods. However, in the present invention, the work-up is preferably carried out, without isolating the salt, liberating the diketone by acidifying the reaction mixture and then isolating the diketone, in accordance with customary methods, for example by means of extraction or distillation. If extraction is used for the isolation, the extraction can be carried out using the solvent previously employed as the medium in the reaction.

Preferably, the process according to the invention, care is preferably taken to ensure that the carboxylic ester (formula I) does not come into contact with the base (formula II) before the cyclopropyl alkyl ketone (formula III) does.

This condition is achieved by the ester component being metered in portions or continuously into the ketone and alcoholate components which have been initially introduced, either in their entirety or in part, where appropriate in one of the solvents. If only partial quantities of the alcoholate and/or ketone are initially introduced, the addition in portions or continuous addition of the remaining quantities should take place such that these two starting compounds are always present in a stoichiometric excess with respect to the carboxylic ester. In this connection, the alkali metal alcoholate can be introduced in the form of a suspension in the inert solvent. The ester and the ketone can also be metered in as mixtures with each other and/or with the solvent.

It is particularly preferred in the process herein described to adapt this mixing to the apparatus available and, for example, to carry it out speedily when appropriate heat dissipation is available, as for example, in double-jacketed metal reactors. At the same time, there is the option of metering in the feed material over a particular period of time, something which can be advantageous, for example, for safety reasons when heat dissipation is poor, as for example, in an enamel reactor, in order to prevent side reactions and consequently losses of yield, due to overheating of the reaction mixture.

If metering is employed, the carboxylic ester is preferably metered in within up to 4 hours, preferably within from 1 to 2 hours. While longer periods of time are possible in principle, they do not provide any particular advantage.

For a process which is used industrially, additional degrees of freedom can be advantageous, and these are achieved, in the process according to the invention, by the possibility of using ester and alcoholate mixtures containing alkoxy groups ($OR^3$) which differ among themselves, since the $OR^3$ groups do not appear in the product. Thus, methyl acetate and ethyl acetate, for example, and sodium and/or potassium methoxide and ethoxide, for example, can be employed simultaneously. The energy liberated during the reaction can also be used for heating the mixture to the reaction temperature.

The present process is of particular importance from the point of view of economy, since it is distinguished from known processes by particularly short reaction times of from about 1 to 4 hours and the high space/time yields associated therewith. In this regard, space/time yields of at least 0.3 mol/l·h, preferably 0.3 mol/l·h–1.5 mol/l·h are possible with the process of the present invention. Cyclopropylalkane-1,3-diones are obtained in yields of >90% of theory when cyclopropyl alkyl ketones are reacted with a carboxylic ester.

Other features of the invention will become apparent in the course of the following descriptions of exemplary embodiments which are given for illustration of the invention, but are not intended to be limiting thereof.

EXAMPLES

Comparative example A 8.4 g (0.1 mol) of CPMK were added to 51.9 g (0.29 mol) of a 39 wt. % solution of potassium methoxide in methanol, after which 17.6 g (0.2 mol) of ethyl acetate were added at 30° C. within the space of 30 minutes. After 24 h, there was still no sign of CPMK reacting.

Example 1

Preparation of 1-cyclopropylbutane-1,3-dione 14.2 g (0.2 mol) of potassium methoxide were suspended in 75 ml of methyl tert-butyl ether, 8.4 g (0.1 mol) of CPMK were added, and 17.6 g (0.2 mol) of ethyl acetate were metered in within the space of 45 minutes. After 3 h at 30° C., the reaction mixture was worked up with aqueous hydrochloric acid and the low-boiling point constituents were distilled off after extraction. Yield of crude product: 12.18 g, corresponding to 97.4% of theory, purity: 98.5% by weight.

Example 2

Preparation of 1-cyclopropylbutane-1,3-dione

The preparation was carried out in an analogous manner to Example 1, but with the addition of different alcohols to the reaction mixture. The quantities in ml per mole of alcoholate, and the yields are given in Table 1.

TABLE 1

| Alcohol | Quantity (ml/mol) | Yield (% of theory) |
| --- | --- | --- |
| tert-butanol | 50 | 84 |
| polyethylene glycol | 59 | 77 |
| 2-phenoxyethanol | 25 | 84 |
| methanol | 12.5 | 80 |
| ethylene glycol | 25 | 60 |

Example 3

Preparation of
1-Cyclopropyl-4-phenylbutane-1,3-dione

In an analogous manner to Example 1, ethyl phenylacetate was reacted with CPMK. Yield: 80% of theory.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States:

1. A process for preparing a 1-cyclopropylalkane-1,3-dione of formula IV, comprising reacting a cyclopropyl ketone of formula III, an alkali metal alcoholate of formula II and a carboxylic ester of the formula I as shown below

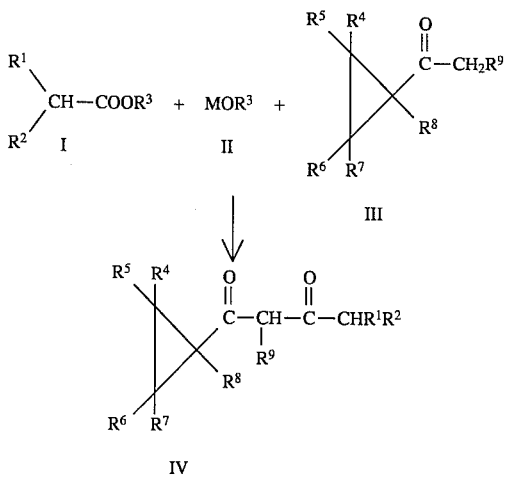

wherein $R^1$, $R^2$ and $R^4$ to $R^8$ are, independently, hydrogen, an alkyl group having from 1 to 6 carbon atoms or an optionally substituted aryl group having from 6 to 10 carbon atoms, $R^3$ is an alkyl group having from 1 to 10 carbon atoms, M is an alkali metal, and $R^9$ is hydrogen or an alkyl group having from 1 to 20 carbon atoms, wherein said reacting step is conducted for about 1–4 hours and is carried out at a temperature of not more than 50° C. in a solvent selected from the group consisting of aromatic hydrocarbons, aliphatic hydrocarbons, araliphatic hydrocarbons, aromatic halohydrocarbons, ethers, polyethers, esters which are resistant to re-esterification and hydrolysis, amides, amines, said cyclopropyl ketone of formula III, said carboxylic ester of formula I and mixtures thereof which contains from 0 up to 0.7 mol of alcohol per mol of alkali metal of alcoholate.

2. The process of claim 1, comprising reacting 1–5 mol of said alkali metal alcoholate with 1–9 mol of said carboxylic ester per 1 mol of said cyclopropyl ketone.

3. The process of claim 2, comprising reacting 1–2 mol of said alkali metal alcoholate with 1–2 mol of said carboxylic ester per 1 mol of said cyclopropyl ketone.

4. The process of claim 1, wherein said alkali metal alcoholate is selected from the group consisting of sodium methoxide, sodium ethoxide, potassium methoxide, potassium ethoxide and mixtures thereof.

5. The process of claim 2, wherein said alkali metal alcoholate is selected from the group consisting of sodium methoxide, sodium ethoxide, potassium methoxide, potassium ethoxide and mixtures thereof.

6. The process of claim 1, wherein said reacting step is carried out in a temperature range of between –20° and 50° C.

7. The process of claim 6, wherein said reacting step is carried out in a temperature range of between 0° to 40° C.

8. The process of claim 1, wherein $R^1$ and $R^2$ are hydrogen.

9. The process of claim 8, wherein said cyclopropyl ketone is cyclopropylmethylketone.

10. The process of claim 1, wherein $R^3$ is an alkyl group having from 1 to 6 carbon atoms.

11. The process of claim 10, wherein said carboxylic ester is methylacetate or ethylacetate.

12. The process of claim 9, wherein said carboxylic ester is methylacetate or ethylacetate.

13. The process of claim 1, wherein said alkali metal of said alkali metal alcoholate is selected from the group consisting of lithium, sodium, potassium, rubidium and cesium.

14. The process of claim 13, wherein said alkali metal of said alkali metal alcoholate is sodium or potassium.

15. A process for preparing a 1-cyclopropylalkane-1,3-dione of formula IV, comprising reacting a cyclopropyl ketone of formula III, an alkali metal alcoholate of formula II and a carboxylic ester of the formula I as shown below

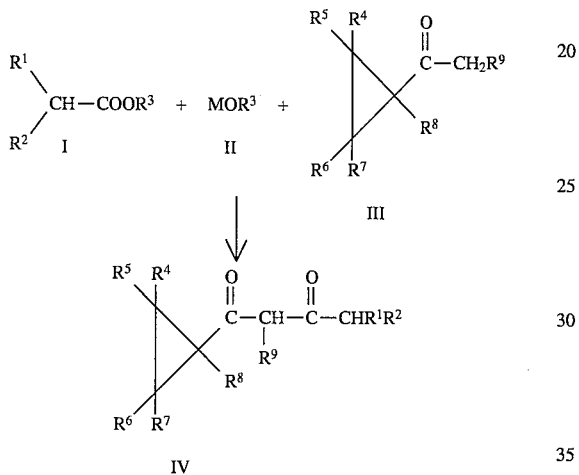

wherein $R^1$, $R^2$ and $R^4$ to $R^8$ are, independently, hydrogen, an alkyl group having from 1 to 6 carbon atoms or an optionally substituted aryl group having from 6 to 10 carbon atoms, $R^3$ is an alkyl group having from 1 to 10 carbon atoms, M is an alkali metal, and $R^9$ is hydrogen or an alkyl group having from 1 to 20 carbon atoms, wherein said reacting step is conducted for about 1–4 hours and is carried out at a temperature of not more than 50° C. in a solvent selected from the group consisting of aromatic hydrocarbons, aliphatic hydrocarbons, araliphatic hydrocarbons, aromatic halohydrocarbons, ethers, polyethers, esters which are resistant to re-esterification and hydrolysis, amides, amines, said cyclopropyl ketone of formula III, said carboxylic ester of formula I and mixtures thereof which contains from 0 up to 0.7 mol of alcohol per mol of alkali metal of alcoholate, wherein said reacting step comprises contacting said alkali metal alcoholate with said cyclopropyl ketone to form a mixture and then contacting said mixture with said carboxylic ester.

16. A process for preparing a 1-cyclopropylalkane-1,3-dione of formula IV, comprising reacting a cyclopropyl ketone of formula III, an alkali metal alcoholate of formula II and a carboxylic ester of the formula I as shown below

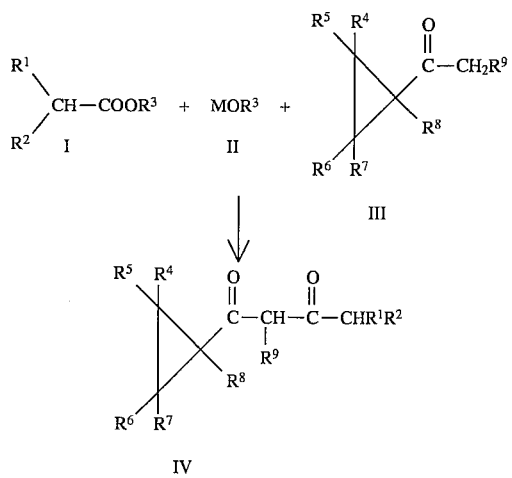

wherein $R^1$, $R^2$ and $R^4$ to $R^8$ are, independently, hydrogen, an alkyl group having from 1 to 6 carbon atoms or an optionally substituted aryl group having from 6 to 10 carbon atoms, $R^3$ is an alkyl group having from 1 to 10 carbon atoms, M is an alkali metal, and $R^9$ is hydrogen or an alkyl group having from 1 to 20 carbon atoms, wherein said reacting step is conducted for about 1–4 hours and is carried out at a temperature of not more than 50° C. in a solvent selected from the group consisting of aromatic hydrocarbons, aliphatic hydrocarbons, araliphatic hydrocarbons, aromatic halohydrocarbons, ethers, polyethers, esters which are resistant to re-esterification and hydrolysis, amides, amines, said cyclopropyl ketone of formula III, said carboxylic ester of formula I and mixtures thereof which contains from 0 up to 0.7 mol of alcohol per mol of alkali metal of alcoholate, wherein $R^1$ and $R^2$ are hydrogen, said cyclopropyl ketone is cyclopropyl methyl ketone, and wherein said reacting step comprises contacting said alkali metal alcoholate with said cyclopropyl methyl ketone to form a mixture and then contacting said mixture with said carboxylic ester, wherein said carboxylic ester is an acetic ester.

17. The process of claim 1, wherein said solvent contains no alcohol.

18. The process of claim 1, wherein said solvent contains an alcohol selected from the group consisting of $C_{1-10}$ aliphatic alcohols, $C_{7-15}$ araliphatic alcohols, poly $C_{2-4}$ alkylene glycols and poly $C_{2-4}$ alkylene glycol ethers.

19. The process of claim 1, wherein said solvent is said cyclopropyl ketone of formula III, said carboxylic ester of formula I or a mixture thereof.

20. The process of claim 19, wherein said solvent is said carboxylic ester of formula I.

* * * * *